United States Patent [19]

Herd et al.

[11] Patent Number: 4,659,827

[45] Date of Patent: Apr. 21, 1987

[54] PROCESS FOR PRODUCING 2,4,5,6-TETRACHLOROPYRIMIDINE BY WAY OF 5,6-DICHLORO-2,4-DIHYDROXYPYRIMIDINE WHICH WAS PRODUCED FROM THE CORRESPONDING 5,6-DICHLORO-2,4-DI(TRIHALOMETHYL)-PYRIMIDINE AND A PROCESS FOR PRODUCING 2,4-DIHYDROXYPYRIMIDINE DERIVATIVES

[75] Inventors: Karl J. Herd, Odenthal; Karl H. Schündehütte, Leverkusen, both of Fed. Rep. of Germany

[73] Assignee: Bayer Aktiengesellschaft, Leverkusen, Fed. Rep. of Germany

[21] Appl. No.: 795,390

[22] Filed: Nov. 6, 1985

[30] Foreign Application Priority Data

Nov. 16, 1984 [DE] Fed. Rep. of Germany ....... 3441935

[51] Int. Cl.[4] .................. C07D 239/30; C07D 239/36; C07D 239/54; C07D 239/62
[52] U.S. Cl. .................. 544/299; 544/303; 544/309; 544/313; 544/334
[58] Field of Search ............... 544/299, 303, 309, 313, 544/319, 334

[56] References Cited

U.S. PATENT DOCUMENTS 3,290,306 12/1966 Schmidt et al. .................. 544/334

FOREIGN PATENT DOCUMENTS 0048293 6/1962 Poland ................. 544/334

OTHER PUBLICATIONS

Daiichi, Abstract JP 42-14952, 8/19/1967.

*Primary Examiner*—Henry H. Jilet
*Assistant Examiner*—J. G. Mullins
*Attorney, Agent, or Firm*—Sprung Horn Kramer & Woods

[57] ABSTRACT 2,4-Dihydroxypyrimidines of the formula

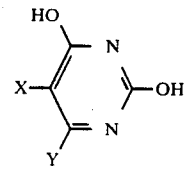

with the substituent meanings given in the description, are obtained by reacting pyrimidines of the formula

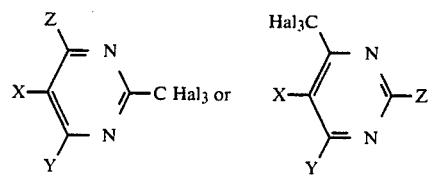

with the substituent meanings given in the description, with aqueous alkalis at elevated temperature. 2,4,5,6-Tetrachloropyrimidine is obtained from the dihydroxypyrimidines by reaction with agents which replace hydroxyl by chlorine.

6 Claims, No Drawings

PROCESS FOR PRODUCING 2,4,5,6-TETRACHLOROPYRIMIDINE BY WAY OF 5,6-DICHLORO-2,4-DIHYDROXYPYRIMIDINE WHICH WAS PRODUCED FROM THE CORRESPONDING 5,6-DICHLORO-2,4-DI(TRIHALOMETHYL)-PYRIMIDINE AND A PROCESS FOR PRODUCING 2,4-DIHYDROXYPYRIMIDINE DERIVATIVES

The present invention relates to a process for the preparation of 2,4-dihydroxypyrimidines (1H, 3H-2,4-pyrimidinediones), which in one of the possible tautomeric forms, correspond to the formula

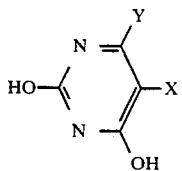

wherein
X=H, Cl, Br or optionally substituted $C_1$–$C_4$-alkyl and
Y=X or OH.

Preferably, X represents Cl or Br and Y represents Cl.

The new preparation process for the compounds (1) comprises heating tetrahalogenomethyl compounds of the formula (2) or (3)

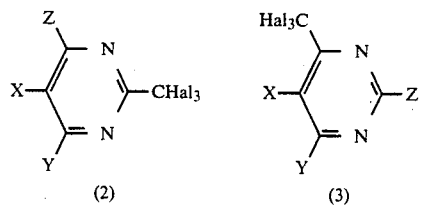

wherein
Hal=Cl or Br,
Z=Hal or hydroxyl and
X and Y have the abovementioned meaning, in an aqueous-alkaline medium, if appropriate under pressure. If appropriate, water-miscible solvents, such as sulpholane, acetonitrile, dimethylsulphoxide or dimethylformamide, can also be used in this reaction.

The reaction is preferably carried out with about 10–50% strength sodium hydroxide solution or potassium hydroxide solution, in particular with about 10–30% strength sodium hydroxide solution, at temperatures between 60° and 110° C. Under these reaction conditions, the halo form liberated during the reaction is hydrolysed directly.

The compounds (2) and (3) are known from the literature or can be prepared by processes which are known from the literature.

The 2,4-dihydroxypyrimidines (1) are useful intermediates for the preparation of chlorine-containing or fluorine-containing pyrimidines, such as 2,4,5,6-tetrachloropyrimidine or 5-chloro-2,4,6-trifluoropyrimidine, which are of importance as reactive components in dyestuff chemistry and which are obtained by reacting (1) with, for example, phosphorus oxychloride, phosphorus pentachloride, phosphorus trichloride, thionyl chloride, phosgene or similar reagents which replace hydroxyl by chlorine.

The new process is particularly used for the preparation of the following dihydroxypyrimidines of the formula (1): 5,6-dichloro-2,4-dihydroxypyrimidine, 6-chloro-2,4-dihydroxypyrimidine, 5-bromo-6-chloro-2,4-dihydroxypyrimidine, 6-chloro-5-methyl-2,4-dihydroxypyrimidine and 5,6-dibromo-2,4-dihydroxypyrimidine.

Details for the preparation are given in the examples.

If high concentrations are used, in particular high alkali concentrations, dimers and/or trimers may initially form, and these hydrolyse to the monomeric compounds as the reaction time advances or by dilution of the reaction mixture.

The following trihalogenomethylpyrimidines (2) or (3) are preferably of interest as starting compounds for the preparation process: 4,5,6-trichloro-2-trichloromethylpyrimidine, 2,5,6-trichloro-4-trichloromethylpyrimidine, 4,6-dichloro-2-trichloromethylpyrimidine, 2,6-dichloro-4-trichloromethylpyrimidine, 5,6-dichloro-4-hydroxy-2-trichloromethylpyrimidine, 5-bromo-4,6-dichloro-2-trichloromethylpyrimidine, 6-chloro-4-hydroxy-2-trichloromethylpyrimidine, 6-chloro-2-hydroxy-4-trichloromethylpyrimidine, 5,6-dichloro-2-hydroxy-4-trichloromethylpyrimidine, 2,6-dichloro-5-methyl-4-trichloromethylpyrimidine, 5-bromo-6-chloro-4-hydroxy-2-trichloromethylpyrimidine and 4,5,6-tribromo-2-tribromomethylpyrimidine.

EXAMPLE 1

5,6-Dichloro-2,4-dihydroxypyrimidine from 4,5,6-trichloro-2-trichloromethylpyrimidine (A) 242 g of molten 4,5,6-trichloro-2-trichloromethylpyrimidine are metered into a mixture, warmed to 75°–80° C., of 1,200 ml of water, 600 ml of 50% strength sodium hydroxide solution and 15 ml of an emulsifier solution over a heated dropping funnel in the course of 1.5 hours. A rise in temperature to 95° C. is to be observed as a result of exothermic heat of reaction. A clear amber-coloured solution results. After a further hour at 90°–95° C., the reaction solution is cooled and brought to pH 6 with hydrochloric acid. The product which has crystallised out is filtered off with suction, rinsed with about 70 ml of water and dried. 119 g (82% of theory) of a sand-coloured crystalline substance of melting point 302°–303° C. (decomposition) are obtained. The substance proves to be identical, by comparison of the IR and melting point, to 5,6-dichloro-2,4-dihydroxypyrimidine, which was obtained by hydrolysis of 2,4,5,6-tetrachloropyrimidine according to German Offenlegungsschrift 2,153,511. A small amount of 5,6-dichloro-4-hydroxy-2-pyrimidinecarboxylic acid is detectable in the filtrate.

(B) 500 g of an approximately 50% strength solution of 4,5,6-dichloro-2-trichloromethylpyrimidine in sulpholane are slowly added dropwise to 1,000 ml of 40% strength sodium hydroxide solution, which has been warmed to 70° C. The mixture is stirred at 90° C. for a further hour. Deposition of oligomeric intermediates is to be observed during this period. 2 l of water are added and the reaction mixture is warmed, while cooling under reflux, until a relatively clear solution results. After cooling, neutralising, filtering with suction and drying analogously to variant (A), 115 g of 5,6-dichloro-2,4-dihydroxpyrimidine are isolated.

EXAMPLE 2

5,6-Dichloro-2,4-dihydroxypryimidine from 2,5,6-trichloro-4-trichloromethylpyrimidine 120 g of 2,5,6-trichloromethylpyrimidine are added in portions to a solution of 1,000 ml of water, 500 ml of 40% strength potassium hydroxide solution and 10 ml of emulsifier solution at 70° C. After a further hour at 65°-70° C., the warm reaction solution is clarified, cooled and acidified to pH 4. After isolation and drying, 57 g (79% of theory) of 5,6-dichloro-2,4-hydroxypyrimidine are obtained.

EXAMPLE 3

6-Chloro-2,4-dihydroxypyrimidine from 4,6-dichloro-2-trichloromethylpyrimidine 10 g of 4,6-dichloro-2-trichloromethylpyrimidine are warmed to 90° C. in 50 ml of concentrated sodium hydroxide solution and 100 ml of water, with addition of an emulsifier. A two-phase system temporarily occurs, and later a precipitate and finally a cloudy solution result. After stirring at 90° C. for a further 30 minutes, the mixture is cooled to 50° C. and clarified and the solution is neutralised with hydrochloric acid. The solution is then concentrated until crystallisation starts and is cooled in an ice-bath or filtered out with 20 g of sodium chloride. The crystalline product is filtered off with suction, washed with a little ice-water and dried. 3.7 g (68% of theory) of 6-chloro-2,4-dihydroxypyrimidine of melting point 300° C. (decomposition) (compare J. Chem. Soc. 1960, 4771) are obtained.

EXAMPLE 4

5,6-Dichloro-2,4-dihydroxypyrimidine from 5,6-dichloro-4-hydroxy-2-trichloromethylpyrimidine 282.5 g of 5,6-dichloro-4-hydroxy-2-trichloromethylpyrimidine which has been melted at 120° C. are slowly introduced into an amount of 600 ml of 40% strength sodium hydroxide solution, which has been warmed to 100°-108° C. The reaction solution is kept constantly at the reflux temperature by the heat of reaction liberated. The introduction period is 2 hours. The reaction has then also ended. The mixture is cooled to 25° C. and brought to pH 5 with 100 ml of hydrochloric acid. The pale yellow product which has precipitated out is filtered off with suction and dried. The yield of 5,6-dichloro-2,4-dihydroxypyrimidine is 163 g (90% of theory).

EXAMPLE 5

2,4,5,6-Tetrachloropyrimidine (TCP)

163 g of 5,6-dichloro-2,4-dihydroxypyrimidine are introduced into a mixture of 230 g of phosphorus oxychloride, 25 g of phosphorus trichloride and 10 g of tri-n-butylamine and the mixture is warmed under reflux for 6 hours, until the temperature in the vapour phase rises to 110° C. 300 g of phosphorus trichloride and 125 g of chlorine are slowly and simultaneously passed in over a period of 10 hours. Finally, a further 19 g of chlorine are added and the mixture is warmed for a further hour, during which the temperature reaches 117° C. Phosphorus oxychloride is first distilled off from the clear solution and the tetrachloropyrimidine is then fractionated in vacuo. The yield is 183 g.

What is claimed is:

1. Process for the preparation of 2,4-dihydroxypyrimidines which, in one of the possible tautomeric forms, correspond to the formula

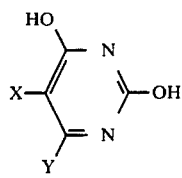

wherein
X=H, Cl, Br or $C_1$-$C_4$-alkyl and
Y=X or OH,
characterised in that pyrimidines of the formula

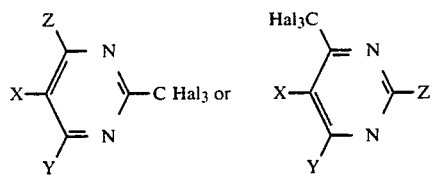

wherein
Hal=Cl or Br and
Z=Hal or OH,
are heated in an aqueous-alkaline medium.

2. Process according to claim 1, characterised in that the reaction is carried out at about 60°-110° C. with about 10-50% strength NaOH or KOH.

3. Process for the preparation of 2,4,5,6-tetrachloropyrimidine, characterised in that 5,6-dichloro-2,4-dihydroxypyrimidine is prepared according to claim 1 and is reacted in a further step with reagents which replace hydroxyl groups.

4. Process for the preparation of 2,4,5,6-tetrachloropyrimidine, characterised in that 5,6-dichloro-2,4-dihydroxypyrimidine is prepared according to claim 2 and is reacted in a further step with reagents which replace hydroxyl groups.

5. Process for the preparation of 2,4,5,6-tetrachloropyrimidine, characterised in that 5,6-dichloro-2,4-dihydroxypyrimidine is prepared according to claim 1 and is further reacted with phosphorus pentachloride, phosphorus trichloride, phosphorous oxychloride, thionyl chloride, or phosgene to replace the hydroxyl with chlorine.

6. Process for the preparation of 2,4,5,6-tetrachloropyrimidine, characterised in that 5,6-dichloro-2,4-dihydroxypyrimidine is prepared according to claim 2 and is further reacted with phosphorus pentachloride, phosphorus trichloride, phosphorus oxychloride, thionyl chloride, or phosgene to replace the hydroxyl with chlorine.

* * * * *